(12) United States Patent
Hesels et al.

(10) Patent No.: US 11,360,165 B2
(45) Date of Patent: Jun. 14, 2022

(54) METHOD FOR POSITIONING OF AN ACCESSORY UNIT ON A PATIENT FOR A MAGNETIC RESONANCE EXAMINATION

(71) Applicant: Siemens Healthcare GmbH, Erlangen (DE)

(72) Inventors: Katharina Hesels, Erlangen (DE); Jonas Vollmer, Erlangen (DE); Sabine Norosinski, Spardorf (DE); George William Ferguson, Erlangen (DE); Roman Achleitner, Nuremberg (DE)

(73) Assignees: Siemens Healthcare GmbH, Erlangen (DE); Designaffairs GmbH, Munich (DE)

( * ) Notice: Subject to any disclaimer, the term of this patent is extended or adjusted under 35 U.S.C. 154(b) by 473 days.

(21) Appl. No.: 16/415,158

(22) Filed: May 17, 2019

(65) Prior Publication Data
US 2019/0353719 A1 Nov. 21, 2019

(30) Foreign Application Priority Data
May 18, 2018 (EP) .................................. 18173169

(51) Int. Cl.
*G01R 33/28* (2006.01)
*G01R 33/30* (2006.01)
*G01R 33/34* (2006.01)
*A61B 5/055* (2006.01)

(52) U.S. Cl.
CPC ............ *G01R 33/283* (2013.01); *A61B 5/055* (2013.01); *G01R 33/307* (2013.01); *G01R 33/34084* (2013.01)

(58) Field of Classification Search
CPC ................ G01R 33/283; G01R 33/307; G01R 33/34084
See application file for complete search history.

(56) References Cited

U.S. PATENT DOCUMENTS

| 2013/0342851 | A1 | 12/2013 | Dresel et al. |
| 2015/0293188 | A1* | 10/2015 | Haider ............. G01R 33/34084 324/307 |
| 2016/0074003 | A1 | 3/2016 | Manke et al. |

(Continued)

FOREIGN PATENT DOCUMENTS

| DE | 102012209190 A1 | 12/2013 |
| DE | 102015211148 A1 | 12/2016 |

(Continued)

OTHER PUBLICATIONS

European Search Report dated Nov. 22, 2018—European Application No. 18173169.6.

*Primary Examiner* — G. M. A Hyder
(74) *Attorney, Agent, or Firm* — Banner & Witcoff Ltd.

(57) ABSTRACT

Techniques are disclosed for assisting in positioning an accessory unit on a patient for a magnetic resonance examination. Also disclosed is a magnetic resonance apparatus, which is designed to perform a method for assisting in positioning an accessory unit on a patient for a magnetic resonance examination. A corresponding computer program product is also disclosed, which is designed to perform a method for assisting in positioning an accessory unit on a patient for a magnetic resonance examination, and an electronically readable data storage medium containing the computer program.

20 Claims, 3 Drawing Sheets

(56) References Cited

U.S. PATENT DOCUMENTS

| | | | |
|---|---|---|---|
| 2016/0367169 A1 | 12/2016 | Hardie et al. | |
| 2017/0209110 A1 | 7/2017 | Kiraly | |
| 2017/0328967 A1 | 11/2017 | Keil | |
| 2017/0343636 A1 | 11/2017 | Kroell | |
| 2018/0116518 A1 | 5/2018 | Rinck et al. | |
| 2018/0314891 A1* | 11/2018 | Ota | H04N 9/3185 |
| 2019/0274582 A1* | 9/2019 | Zeller | A61B 5/055 |

FOREIGN PATENT DOCUMENTS

| | | |
|---|---|---|
| DE | 102016208018 A1 | 11/2017 |
| DE | 102016209297 A1 | 11/2017 |
| EP | 3315986 A1 | 5/2018 |

\* cited by examiner

METHOD FOR POSITIONING OF AN ACCESSORY UNIT ON A PATIENT FOR A MAGNETIC RESONANCE EXAMINATION

CROSS-REFERENCE TO RELATED APPLICATIONS

The present application claims the benefit of the filing date of EP application no. 18173169.6, filed on May 18, 2018, the contents of which are incorporated herein by reference in their entirety.

TECHNICAL FIELD

The present disclosure relates to a method for assisting in positioning an accessory unit on a patient for a magnetic resonance examination, to a magnetic resonance apparatus, which is designed to perform a method for assisting in positioning an accessory unit on a patient for a magnetic resonance examination, to a corresponding computer program product, which is designed to perform a method for assisting in positioning an accessory unit on a patient for a magnetic resonance examination, and to an electronically readable data storage medium containing the computer program.

BACKGROUND

A key factor for image quality in magnetic resonance examinations is ideal and/or optimum positioning of possible accessory units, for instance local radio frequency (RF) antenna units, on the patient, in particular on a region of the patient to be examined. A medical operator positions the accessory unit, and therefore the optimum positioning of the accessory unit often depends on the level of experience of the medical operator. If an inexperienced and/or non-expert medical operator positions the accessory unit, this can result in problems with the positioning and may also lead to problems with the image quality.

SUMMARY OF THE INVENTION

An object of the present disclosure is to make it easier for a medical operator to prepare a patient for a magnetic resonance examination. This object is achieved by the embodiments as described herein. German patent applications DE 10 2016 209 297 A1 and DE 10 2016 208 018 A1 disclose prior positioning techniques.

The disclosure described a method for assisting an accessory unit on a patient for a magnetic resonance examination, which method comprises the following steps: (1) acquiring position data relating to the patient using an acquisition unit; (2) computing an individual required position of the accessory unit using a computing unit, said individual required position for the accessory unit being computed from the position data, examination information, and/or from the data relating to accessory units; and (3) projecting the individual required position of the accessory unit onto the patient using a projection unit, wherein the accessory unit comprises a characteristic pattern, which is projected on the individual required position.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The exemplary embodiments of the present disclosure will be described with reference to the accompanying drawings. The drawing in which an element first appears is typically indicated by the leftmost digit(s) in the corresponding reference number.

DETAILED DESCRIPTION

Figure 1:
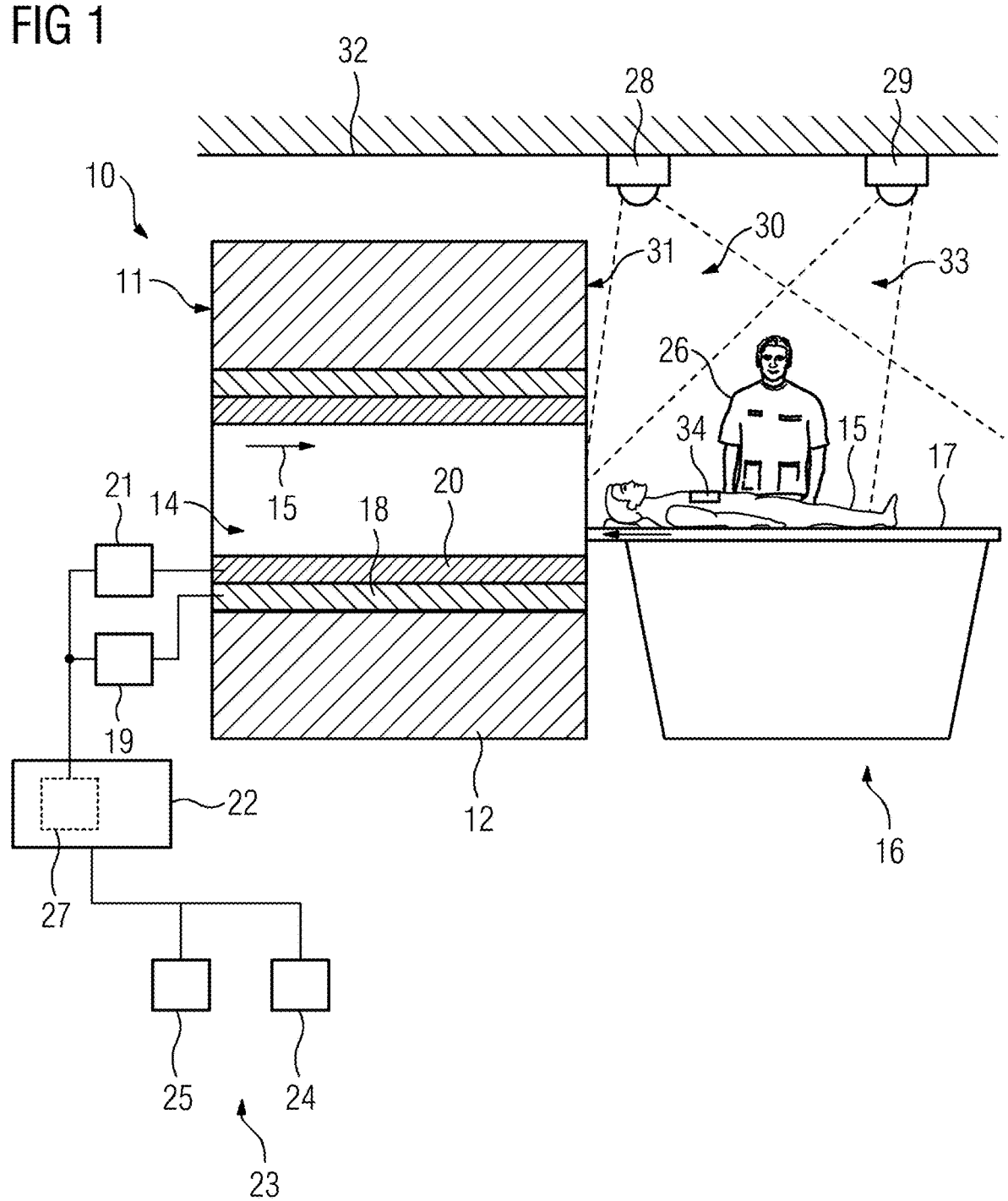
FIG. 1 illustrates a schematic diagram of a magnetic resonance apparatus according to an embodiment of the disclosure.

Before a magnetic resonance examination is started, a medical operator first prepares the patient to be examined. Preparing the patient includes, for example, positioning the patient on a patient support apparatus. Positioning of the patient on the patient support apparatus also depends on a region of the patient to be examined. For example, for a head examination, the patient is placed on the patient support apparatus such that the patient is moved headfirst into a patient placement zone of the magnetic resonance apparatus. For a foot examination and/or a knee examination, however, the patient is placed on the patient support apparatus such that the patient is moved feet-first into a patient placement zone of the magnetic resonance apparatus.

To prepare the patient for the magnetic resonance examination, not only is the patient positioned, but any accessory units that may be required that are also attached to the patient. Examples of such accessory units may be a local RF antenna unit for a magnetic resonance examination on the patient. As other examples, the accessory unit may also include an electrocardiogram (ECG) unit, respiratory sensors, positioning aids (e.g., cushion or preformed foam), and/or other suitable accessory units deemed practical by a person skilled in the art. The medical operator positions these accessory units correctly on the patient, i.e., with the correct orientation and in the correct position.

In embodiments, as further described below, an acquisition unit acquires position data relating to the patient automatically and/or autonomously. The acquisition unit may be, for instance, mounted on a scanner unit of the magnetic resonance apparatus or on a wall or ceiling of an examination room in which the scanner unit of the magnetic resonance apparatus is arranged. The acquisition unit may have an acquisition region that encompasses a region in which the preparation of the patient for the magnetic resonance examination takes place. This acquisition region may encompass a region that is in front of the scanner unit of the magnetic resonance apparatus and/or adjoins a front face of the scanner unit.

The position data relating to the patient may include, for example, a position, orientation, and/or a dimension, such as a size, length, width, and/or a height, of the patient. Alternatively or additionally, the position data relating to the patient can also comprise a position of the patient on the patient support apparatus and/or with respect to the patient support apparatus. Moreover, the position data relating to the patient can also comprise just individual body regions of the patient, such as the body region to be examined of the patient (e.g., dimensions of an arm or of the head or of the torso, etc.).

In an embodiment, the acquired position data relating to the patient is transferred from the acquisition unit to the computing unit via a data transfer unit, for example. It can be the case here that the computing unit retrieves the acquired position data relating to the patient also actively from the acquisition unit. The data can be transferred between the computing unit and the acquisition unit by means of a cable, or wirelessly without a cable.

In an embodiment, the computing unit computes an individual required position of the accessory unit. For instance, the computing unit computes the individual required position of the accessory unit automatically and/or autonomously. The computing unit may include a processor for this purpose. In addition, the computing unit may also include corresponding computing programs and/or computing software, which on execution perform a method for assisting in preparing a patient for a magnetic resonance examination. Said computing programs and/or computing software may be stored inside a memory unit of the computing unit and/or of the magnetic resonance apparatus. In addition, the computing programs and/or computing software can also be stored in an external memory such as the Cloud, for example, in which case the computing unit can access the computing programs and/or computing software by means of a data network. In any case, the computing programs and/or the computing software may be stored in a non-transitory computer readable media having instructions stored thereon such that, when executed by the processors associated with the computing unit, cause the processors (and thus, in turn, the computing unit) to perform the various aspects disclosed herein. The computing unit can be an integral part of a controller of the magnetic resonance apparatus. Alternatively or additionally, the computing unit can also be in the form of an autonomous unit.

In an embodiment, examination information may include, for example, a region of interest and/or region to be examined of the patient. The region of interest may already be stored in a patient database that is accessible to the computing unit. For instance, the region of interest may be acquired already during patient registration, and can be stored in the patient database. It is also conceivable that the region of interest is communicated while the patient is being prepared for the magnetic resonance examination by the medical operator, for instance via manual input of the region of interest. The examination information may also include, for example, symptoms of the patient, on the basis of which region of interest is defined. Defining the region of interest on the basis of symptoms can also be performed automatically and/or autonomously by the computing unit. For example, given symptoms of "the patient has headaches," the region of interest can be defined initially as the head of the patient on the basis of these symptoms.

In various embodiments, the data relating to the accessory units may be stored in a database, with the computing unit being able to access the data relating to the accessory units from the database by means of the data network. The data relating to the accessory units typically comprises a predefined position of the individual accessory units with respect to the patient support apparatus and/or with respect to an average patient. Alternatively or additionally, the data relating to the accessory units can also include a geometry, such as a length, width, and/or height of the individual accessory units.

In an embodiment, the individual required position of the accessory unit may include a required position of the accessory unit on the patient and/or against the patient. The individual required position of the accessory unit thus includes a position of the accessory unit that the accessory unit is meant to adopt, with respect to the patient, during the magnetic resonance examination. The individual required position can include a patient-specific required position, with the desired position of the accessory unit being determined according to the position data relating to the patient, such as according to an anatomy of the patient, for instance.

In an embodiment, a characteristic pattern of the accessory unit shall be understood to mean a pattern on the surface of the accessory unit. The accessory unit can be identified from the pattern on the surface of the accessory unit. Said characteristic pattern can include an irregular pattern, so that it is possible to determine from a pattern segment an exact position and/or orientation of the accessory unit.

In an embodiment, the computed individual required position of the accessory unit may be transferred from the computing unit to the projection unit via a data transfer unit. It can also be the case here that the computing unit actively communicates and/or sends the computed individual required position of the accessory unit to the projection unit. The data can be transferred between the computing unit and the projection unit by means of a cable or wirelessly without a cable.

In an embodiment, the projection unit may project the individual required position of the accessory unit. Said projection unit may be mounted on the scanner unit of the magnetic resonance apparatus or on a wall or ceiling of the examination room, in which the scanner unit of the magnetic resonance apparatus is arranged. A projection region of the projection unit may be directed onto the patient and/or the patient support apparatus while the patient is being prepared for the magnetic resonance examination. This projection region may encompass a region that is in front of the scanner unit of the magnetic resonance apparatus and/or adjoins a front face of the scanner unit. The projection unit may project the position information relating to the subject automatically and/or autonomously.

The embodiments described herein advantageously assist a medical operator while a patient is being prepared for a medical imaging examination. In particular, the embodiments described herein enable providing an inexperienced and/or non-expert medical operator with a simple and time-saving aid for positioning the patient, arranging, positioning accessory units, and/or positioning accessory units. By means of the assistance for optimized placement of the patient and/or of the accessory unit(s) described herein, it is hence possible to prevent incorrect positioning, and thus image quality is advantageously increased. The embodiments described herein may also advantageously obviate repeated measurements resulting from incorrect positioning.

In addition, embodiments include uniquely identifying an accessory unit. For example, the acquisition unit can identify the accessory unit from the detected characteristic pattern, and hence the user can be advantageously shown a positioning suggestion. Alternatively, the user can be offered a suggestion for selecting an accessory unit for the planned examination, with the user able to select the accessory unit on the basis of the characteristic pattern, and hence any confusion over the accessory unit can be avoided.

Advantageously, the embodiments described herein include the acquisition unit comprising a camera. For example, the acquisition unit may be implemented as a 2D camera and/or a 3D camera. This can provide a low-cost acquisition unit for acquiring the position data relating to the patient.

Alternatively or additionally, the acquisition unit can also comprise a sensor unit, which acquires the position data relating to the patient. In this case, the sensor unit can be integrated inside the patient support apparatus, which comprises pressure sensors and/or RF sensors, for example. The sensors may be integrated inside a mattress of the patient support apparatus so that a location, orientation, size, and/or position of the patient can be inferred from a pressure distribution measured via the integrated sensors.

Advantageously, the embodiments described herein include the accessory unit comprising a local RF antenna unit. This facilitates simple and rapid positioning of a local RF antenna unit for a non-expert and/or inexperienced operator.

Advantageously, the embodiments described herein include the position data relating to the patient comprising a contour of the patient. The contour of the patient shall be understood to mean, for instance, an outline of the body of the patient, which contour and/or outline of the patient being determined and/or computed from a patient model. The patient model can comprise, for example, a 2D patient model or a 3D patient model. Consequently, the contour of the patient can comprise a 2D contour or a 3D contour of the patient. This can allow the patient-specific and/or individual required position of the accessory unit to be determined and/or computed with precision. For example, determining the individual required position of the accessory unit can advantageously take into account specific anatomical features of the patient.

Advantageously, the embodiments described herein include the computing unit, which computed the individual required position of the accessory unit, executing an algorithm, which uses the position data relating to the patient to determine a patient-specific required position of the accessory unit. A patient-specific required position shall be understood to mean, for instance, a required position of the accessory unit that is specifically adapted to a figure and/or anatomy of the patient. Thus the algorithm can be used to adapt the individual required position of the accessory unit to the patient in a particularly quick and time-saving manner.

Advantageously, the embodiments described herein include the individual accessory units being distinguishable by their respective characteristic patterns, whereby the associated accessory unit can be identified easily from its characteristic pattern. Moreover, selecting the accessory unit can hence be made simpler for an inexperienced and/or non-expert medical operator.

Advantageously, the embodiments described herein include the characteristic pattern being used to determine the accessory unit. In this case, the computing unit can select the accessory unit on the basis of the region of interest or other patient data, and notify the user of the characteristic pattern. The user can then use the characteristic pattern to select and/or determine the correct accessory unit from the multiplicity of accessory units. Alternatively or additionally, the accessory unit can also be selected by the user, such as by the medical operator, in which case the accessory unit can be determined and/or identified by its characteristic pattern. The characteristic pattern may be detected by the acquisition unit, and the computing unit can hence also define a position, such as the individual required position of the accessory unit.

Advantageously, the embodiments described herein include computing the individual required position of the accessory unit using the computing unit that accesses a database in which the available accessory units may be stored together with characteristic patterns and/or predefined positions for an average patient. It is hence advantageously possible to select and/or compute automatically the individual required position of the accessory unit for all available accessory units. All available accessory units shall be understood to mean, for example, all accessory units that are available and/or present for a magnetic resonance examination locally, i.e. in the location of the magnetic resonance apparatus.

Advantageously, the embodiments described herein include the positioning of the accessory unit being achieved when the projected characteristic pattern matches the characteristic pattern on the accessory unit. Even an inexperienced and/or non-expert medical operator can thereby easily position and/or arrange the accessory unit on the patient.

The embodiments described herein also relate to a magnetic resonance apparatus, which is designed to perform a method for assisting in positioning an accessory unit on a patient for a magnetic resonance examination. The magnetic resonance apparatus may include a scanner unit, a patient support apparatus for supporting the patient for the magnetic resonance examination, an acquisition unit for acquiring position data relating to the patient, a computing unit for computing an individual required position of an accessory unit, and a projection unit for projecting the individual required position of the accessory unit.

The embodiments described herein also advantageously provide assistance to a medical operator while a patient is being prepared for a medical imaging examination. For instance, it is thereby possible to provide an inexperienced and/or non-expert medical operator with a simple and time-saving aid for positioning the patient, arranging positioning accessory units, and/or positioning accessory units. By means of the assistance for optimized placement of the patient and/or of the accessory unit, it is hence possible to prevent incorrect positioning and thus advantageously to increase image quality. This also means that repeat measurements resulting from incorrect positioning can be advantageously avoided.

In addition, embodiments include uniquely identifying an accessory unit. The acquisition unit can identify the accessory unit from the detected characteristic pattern, and hence the user can be advantageously shown a positioning suggestion. Alternatively, the user can be offered a suggestion for selecting an accessory unit for the planned examination, with the user able to select the accessory unit on the basis of the characteristic pattern, and hence any confusion over the accessory unit can be avoided.

The advantages of the magnetic resonance apparatus embodiments are similar to, or essentially the same as, the advantages detailed above for the method embodiments related to assisting in positioning an accessory unit on a patient for a magnetic resonance examination. Features, advantages or alternative embodiments mentioned in this connection can also be applied to the other claimed subject matter, and vice versa.

The embodiment described herein also relate to a computer program product which comprises a program and can be loaded directly in a memory of a programmable system controller of a magnetic resonance apparatus, and which comprises program means for performing a method for assisting in positioning an accessory unit on a patient for a magnetic resonance examination when the program is executed in the system controller of the magnetic resonance apparatus. In addition, the computer program may utilize program means, e.g. libraries and auxiliary functions, for implementing the relevant embodiments of the method. Said computer program can comprise software containing a source code, which may be compiled and linked (or just interpreted), or an executable software code, which for execution may only need to be loaded into a suitable processing unit.

In addition, the embodiment described herein relate to a computer-readable data storage medium (e.g., a non-transitory computer-readable data storage medium), which comprises a program that is intended to perform a method for assisting in positioning an accessory unit on a patient for a magnetic resonance examination.

FIG. 1 illustrates a schematic diagram of a magnetic resonance apparatus according to an embodiment of the disclosure.

FIG. 1 shows a magnetic resonance apparatus 10, which comprises a scanner unit 11 formed by a magnet unit comprising a superconducting main magnet 12 for producing a powerful and substantially constant, main magnetic field 13. The magnetic resonance apparatus 10 also comprises a patient placement zone 14 for accommodating a patient 15. In example embodiment shown in FIG. 1, the patient placement zone 14 is shaped as a cylinder and is enclosed in a circumferential direction cylindrically by the scanner unit 11. However, this is by way of example and not limitation, and the patient placement zone 14 may have a different design of any suitable shape. The patient 15 can be moved and/or shifted into the patient placement zone 14 by a patient support apparatus 16 of the magnetic resonance apparatus 10. The patient support apparatus 16 comprises for this purpose a patient couch 17, which is designed to be able to move inside the patient placement zone 14.

The scanner unit 11 further comprises a gradient coil unit 18 for generating magnetic field gradients, which are used for spatial encoding during imaging. The gradient coil unit 18 is controlled by a gradient controller 19 of the magnetic resonance apparatus 10. The scanner unit 11 further comprises a RF antenna unit 20 for exciting a polarization that establishes itself in the main magnetic field 13 generated by the main magnet 12. The RF antenna unit 20 is controlled by an RF antenna controller 21 of the magnetic resonance apparatus 10 and radiates high-frequency magnetic resonance sequences into an examination space, which is largely formed by a patient placement zone 14 of the magnetic resonance apparatus 10.

The magnetic resonance apparatus 10 comprises a system controller 22 for controlling the main magnet 12, the gradient controller 19, and the radio-frequency antenna controller 21. The system controller 22 centrally controls the magnetic resonance apparatus 10, for instance implementing a predetermined imaging gradient echo sequence. In addition, the system controller 22 comprises an analysis unit (not presented in further detail) for analyzing medical image data acquired during the magnetic resonance examination.

In addition, the magnetic resonance apparatus 10 comprises a user interface 23, which is connected to the system controller 22. Control data such as imaging parameters, for instance, and reconstructed magnetic resonance images can be displayed to a medical operator 26 on a display unit 24, for example on at least one monitor, of the user interface 23. In addition, the user interface 23 comprises an input unit 25, which can be used by the medical operator 26 to enter data and/or parameters during a measurement process.

The magnetic resonance apparatus 10 also comprises a computing unit 27, an acquisition unit 28, and a projection unit 29. A method for assisting in preparing a patient 15 for a magnetic resonance examination can be performed using the computing unit 27, the acquisition unit 28, and the projection unit 29. The method for assisting in preparing a patient 15 for a magnetic resonance examination may be performed automatically and/or autonomously using the magnetic resonance apparatus 10, such as by using the computing unit 27 together with the acquisition unit 28 and the projection unit 29, for example. The computing unit 27 comprises for this purpose a processor, which is not presented in further detail. The computing unit 27 also comprises corresponding computing programs and/or computing software. Said computing programs and/or computing software may be stored inside a memory unit (not presented in further detail) of the computing unit 27 and/or of the magnetic resonance apparatus 10. In addition, the computing programs and/or computing software can also be stored in an external memory such as a Cloud, for example, in which case the computing unit 27 can access the computing programs and/or computing software by means of a data network.

The computing unit 27 can be an integral part of the system controller 22. Alternatively or additionally, the computing unit 27 can also be in the form of an autonomous unit.

In the present embodiment, the acquisition unit 28 is formed by a camera, such as a 2D camera and/or a 3D camera, for example, to acquire 2D position data and/or 3D position data relating to the patient 15. The acquisition unit 28 is arranged inside an examination room, in which the scanner unit 11 is also arranged and/or installed. The acquisition unit 28 is arranged inside the examination room such that an acquisition region 30 of the acquisition unit 28, (e.g., an acquisition region of the camera), covers a region within which preparing the patient 15 for the magnetic resonance examination takes place. This acquisition region 30 and/or this region may lie in front of the scanner unit 11, and directly adjacent to a front face 31 of the scanner unit 11. Said acquisition region 28 may also encompass a location in which the patient support apparatus 16 is situated for preparing the patient 15.

The acquisition unit 28 may be arranged on the scanner unit 11, such as on the front face 31 of the scanner unit 11, for instance. In an embodiment, it may be advantageous for the acquisition unit 28 to be arranged on a wall and/or a ceiling 32 of the examination room, to ensure a continuous unobstructed view onto the patient 15 and/or onto the patient support apparatus 16 while the patient 15 is being prepared for the magnetic resonance examination.

The projection unit 29 is likewise arranged inside the examination room, in which the scanner unit 11 is also arranged and/or installed. The projection unit 29 is arranged inside the examination room such that a projection region 33 of the projection unit 29 covers a region within which preparing the patient 15 for the magnetic resonance examination takes place. This projection region 33 and/or this region may lie in front of the scanner unit 11, and directly adjacent to the front face 31 of the scanner unit 11. Said projection region 33 also encompasses a location in which the patient support apparatus 16 is situated for preparing the patient 15.

The projection unit 29 may be arranged on the scanner unit 11, such as on the front face 31 of the scanner unit 11, for instance In an embodiment, it may be advantageous for the projection unit 29 to be arranged on the wall and/or the ceiling 32 of the examination room, to ensure a continuous unobstructed view onto the patient 15 and/or onto the patient support apparatus 16 while the patient 15 is being prepared for the magnetic resonance examination.

Figure 2:
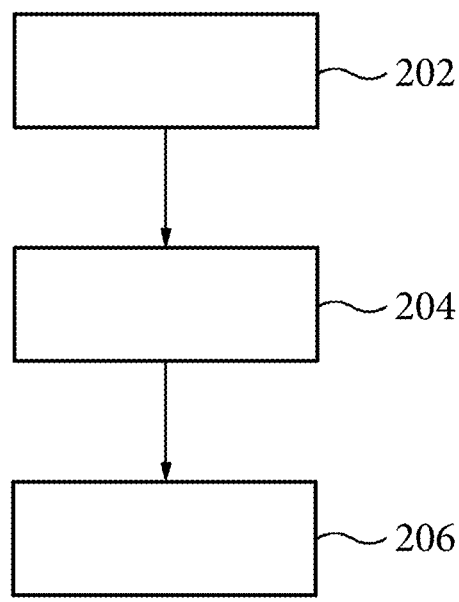
FIG. 2 is an example flow for assisting in positioning an accessory unit on a patient for a magnetic resonance examination, in accordance with an embodiment of the disclosure.
Figure 3:
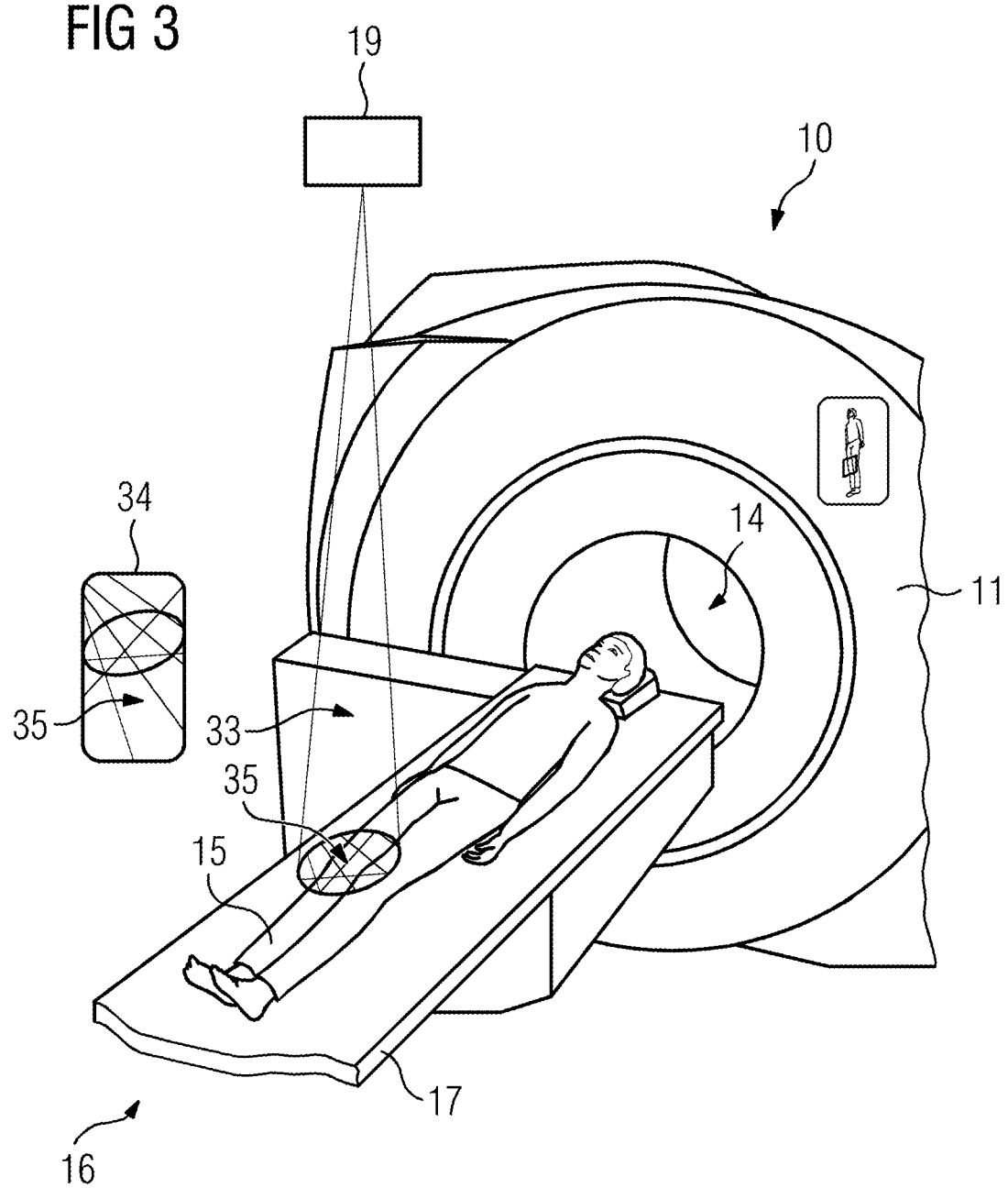
FIG. 3 illustrates a diagram of projecting a characteristic pattern of the accessory unit onto an individual requiring accessory unit positioning, in accordance with an embodiment of the disclosure.

FIG. 2 is an example flow for assisting in positioning an accessory unit on a patient for a magnetic resonance examination, in accordance with an embodiment of the disclosure. With reference to FIGS. 1 and 3, FIG. 2 shows an example flow for assisting in positioning an accessory unit 34 of the magnetic resonance apparatus 10 on a patient 15 for a magnetic resonance examination. At the start of the method, the patient 15 is already positioned on the patient support apparatus 16. The accessory unit 34 comprises a local RF antenna unit, which for the magnetic resonance examination is arranged around the region to be examined of the patient 15. Alternatively or additionally, the accessory unit 34 may also include an ECG unit, an infusion unit, a positioning unit (e.g., a cushion or preformed foam), and/or other suitable units to be arranged on the patient 15 for the magnetic resonance examination.

The flow 200 may include acquiring (block 202) via the acquisition unit 28 position data relating to the patient 15 who is positioned on the patient support apparatus 16. The position data may include, for instance, a contour of the patient 15, such as a 2D contour of the patient 15 or a 3D contour of the patient 15.

The flow 200 may include computing (block 204) via the computing unit 27 an individual required position of the accessory unit 34 on and/or against the patient 15. The individual required position of the accessory unit 34 may be computed from the position data relating to the patient 15. In addition, examination information, for instance information about an examination region of the patient 15 and/or data relating to the accessory units 34, can also be included in the computation of the individual required position of the accessory unit 34.

The data relating to the accessory units 34 may include, for example, a suggested position for the accessory unit 34, which can include a predefined position adapted to an average patient. This suggested position and/or the predefined position adapted to an average patient may take into account the body region of average patients but may not take into account the individual specific anatomical features of the individual patient 15. The data relating to the accessory units 34 may be stored in a database, which is accessible to the computing unit 27 for computing the individual required position of the accessory unit 34.

As shown in greater detail in FIG. 3, the individual accessory units 34 each may have a surface comprising a characteristic pattern 35, which is used to identify the accessory unit 34. For this purpose, the characteristic patterns 35 of the individual accessory units 34 differ from one another, as noted above. For instance, all the available accessory units 34 may be stored in the database together with their respective associated characteristic patterns 35. In addition, also stored in the database may be the data relating to all the available accessory units 34 together with the suggested position associated with each of said accessory units and/or together with the predefined position adapted to an average patient.

The computing unit 27 may comprise or execute, for computing the individual required position of the accessory unit 34, an algorithm (e.g., a computing algorithm stored on non-transitory computer readable media), which uses the position data relating to the patient 15 to determine a patient-specific individual required position of the accessory unit 34. For this purpose, the position data, such as the 2D position data and/or the 3D position data, for instance, relating to the patient 15 may be used to determine a contour (e.g., a 2D contour and/or a 3D contour), and/or an outline (e.g., a 2D outline and/or a 3D outline), of the patient 15, and/or a patient model (e.g., a 2D patient model and/or a 3D patient model). The suggested position and/or the predefined position, which has been adapted to an average patient, of the accessory unit 34, may be stored in the database and may be adjusted individually to suit the contour and/or the outline of the patient 15 and/or of the patient model.

The selection of the appropriate accessory unit 34 required for the forthcoming magnetic resonance examination of the patient 15 can be selected automatically and/or autonomously by the computing unit 27. For instance, this can involve the computing unit 27 using the position data relating to the patient 15 and/or using the examination information to define and/or determine a body region to be examined of the patient 15, and the computing unit 27 then selecting an accessory unit 34 suitable for this body region, such as the appropriate local RF antenna unit, for example. To provide an illustrative example, if the head of the patient is the region to be examined, then the computing unit 27 can select an RF head antenna unit configured for the head as the appropriate accessory unit 34.

It may also be the case that the medical operator 26 has already selected and/or defined the accessory unit 34. In this case, the computing unit 27 can identify the accessory unit 34 from the characteristic pattern 35, for which purpose the acquisition unit 28 detects the accessory unit 34. The computing unit 27 may then adjust the suggested position stored in the database and/or the stored predefined position, which has been adapted to an average patient, of the accessory unit 34 individually to suit the contour and/or the outline of the patient 15 and/or of the patient model.

The flow 200 may include projecting (block 206) via the projection unit 29 the individual required position of the accessory unit 34 on the patient 15, such as on a surface of the patient 15, for example. The accessory unit 34 may include, or be associated with, the characteristic pattern 35, which is projected onto the individual required position of the accessory unit 34. In this process, the medical operator 26 positions the accessory unit 34, with the medical operator 26 moving or repositioning the accessory unit 34 until the characteristic pattern 35 on the surface of the accessory unit 34 matches the characteristic pattern 35 projected onto the patient 15.

If the computing (block 204) of the individual required position is performed via the computing unit 27 that selects the accessory unit 34 using the position data relating to the patient 15 and/or using examination information, then the projection (block 206) may include the medical operator 26 additionally being shown which accessory unit 34 is meant to be used for the forthcoming magnetic resonance examination. It is then possible for the medical operator 26 to determine and/or to select the accessory unit 34 particularly easily using the projected characteristic pattern 35.

Although the embodiments have been illustrated and described in detail using examples, the embodiments are not limited by the disclosed examples, and a person skilled in the art can derive other variations therefrom without departing from the scope of protection of the disclosure. Furthermore, although modifications and changes may be suggested by those skilled in the art, it is the intention to embody all changes and modifications as reasonably and properly come within the scope of their contribution to the art.

What is claimed is:

1. A method for assisting in positioning an accessory unit on a patient for a magnetic resonance examination, comprising:

acquiring, via position acquisition circuitry, position data relating to the patient while the patient is situated on a patient support associated with a magnetic resonance scanner with which the magnetic resonance examination is to be performed, the magnetic resonance examination using an accessory unit that is placed on the patient;

computing, via processing circuitry, a required position of the accessory unit on the patient for the magnetic resonance examination, the required position for the accessory unit being computed using one or more of (i) the position data, (ii) examination information related to the magnetic resonance examination, and (iii) data related to the accessory used for the magnetic resonance examination; and projecting, via projection circuitry in communication with the computing unit, a characteristic pattern, which is associated with a characteristic pattern disposed on a surface of the accessory, at the computed required position onto the patient while the patient is situated on the patient support.

2. The method as claimed in claim 1, wherein the position acquisition circuitry comprises a camera.

3. The method as claimed in claim 1, wherein the accessory comprises a local radiofrequency (RF) antenna unit.

4. The method as claimed in claim 1, wherein the position data relating to the patient comprises a contour of the patient.

5. The method as claimed in claim 1, wherein the act of computing the required position of the accessory includes using the position data relating to the patient to determine a patient-specific required position of the accessory.

6. The method as claimed in claim 1, wherein the accessory is from among a plurality of accessors used for the magnetic resonance examination, and wherein each respective one of the plurality of accessories is distinguished by a respective characteristic pattern.

7. The method as claimed in claim 1, wherein the characteristic pattern is used to determine the accessory.

8. The method as claimed in claim 1, wherein the act of computing the required position of the accessory includes accessing, via the processing circuitry, a database storing available accessories and respective characteristic patterns associated with each of the available accessories.

9. The method as claimed in claim 1, wherein the act of computing the required position of the accessory includes accessing, via the processing circuitry, a database storing available accessories and respective predefined positions for a patient for each of the available accessories.

10. The method as claimed in claim 1, wherein positioning of the accessory is achieved when the projected characteristic pattern matches the characteristic pattern on the accessory.

11. A magnetic resonance apparatus for assisting in positioning an accessory on a patient for a magnetic resonance examination, the magnetic resonance apparatus comprising:

a magnetic resonance scanner configured to receive a patient support that supports a patient for performance of the magnetic resonance examination, the magnetic resonance examination using an accessory that is placed on the patient;

position acquisition circuitry configured to acquire position data relating to the patient while the patient is situated on the patient support for the magnetic resonance examination;

processing circuitry configured to compute a required position of the accessory on the patient for the magnetic resonance examination; and projection circuitry configured to project a characteristic pattern, which is associated with a characteristic pattern disposed on a surface of the accessory, at the computed required position of the accessory onto the patient while the patient is situated on the patient support.

12. The magnetic resonance apparatus of claim 11, wherein the processing circuitry is configured to compute the required position for the accessory onto the patient while the patient is situated on the patient support using one or more of (i) the position data, (ii) examination information related to the magnetic resonance examination, and (iii) data relating the accessory used for the magnetic resonance examination.

13. The magnetic resonance apparatus of claim 11, wherein the accessory is associated with a corresponding characteristic pattern that is projected onto the patient as the required position of the accessory while the patient is situated on the patient support.

14. The magnetic resonance apparatus of claim 11, wherein the processing circuitry is configured to compute the required position of the accessory by accessing a database storing available accessories for the magnetic resonance examination and respective characteristic patterns associated with each of the available accessories.

15. The magnetic resonance apparatus of claim 11, wherein the processing circuitry is configured to compute the required position of the accessory by accessing a database storing the available accessories and respective predefined positions for a patient for each of the available accessories.

16. A non-transitory computer-readable media associated with a magnetic resonance apparatus for assisting in positioning an accessory on a patient while the patient is situated on a patient support for a magnetic resonance examination, the computer-readable media having instructions stored thereon that, when executed by one of more processors, cause the one or more processors to:

acquire position data relating to the patient while situated on the patient support for the magnetic resonance examination;

compute a required position of the accessory unit on the patient for the magnetic resonance examination; and project a characteristic pattern, which is associated with a characteristic pattern disposed on a surface of the accessory unit, at the computed required position of the accessory onto the patient while the patient is situated on the patient support.

17. The non-transitory computer-readable media of claim 16, wherein the media includes instructions that, when executed by one of more processors, cause the one or more processors to compute the required position for the accessory onto the patient while the patient is situated on the patient support using one or more of (i) the position data, (ii) examination information related to the magnetic resonance examination, and (iii) data relating the accessory used for the magnetic resonance examination.

18. The non-transitory computer-readable media of claim 16, wherein the accessory is associated with a corresponding characteristic pattern that is projected onto the patient as the required position of the accessory while the patient is situated on the patient support.

19. The non-transitory computer-readable media of claim 16, wherein the media includes instructions that, when executed by one of more processors, cause the one or more processors to compute the required position of the accessory by accessing a database storing available accessories for the magnetic resonance examination and respective characteristic patterns associated with each of the available accessories.

20. The non-transitory computer-readable media of claim 16, wherein the media includes instructions that, when executed by one of more processors, cause the one or more processors to compute the required position of the accessory by accessing a database storing the available accessories and respective predefined positions for a patient for each of the available accessories.

\* \* \* \* \*